(12) United States Patent
Müller

(10) Patent No.: US 6,676,962 B1
(45) Date of Patent: Jan. 13, 2004

(54) TOPICAL PLASTER WITH NON-STEROIDAL ANTIRHEUMATIC AGENTS WITH AN ACID GROUP

(75) Inventor: Walter Müller, Neuwied (DE)

(73) Assignee: LTS Lohmann Therapie-Systeme, AG (DE)

( * ) Notice: Subject to any disclaimer, the term of this patent is extended or adjusted under 35 U.S.C. 154(b) by 0 days.

(21) Appl. No.: 09/743,124

(22) PCT Filed: Jul. 6, 1999

(86) PCT No.: PCT/EP99/04686
§ 371 (c)(1),
(2), (4) Date: Mar. 1, 2001

(87) PCT Pub. No.: WO00/02539
PCT Pub. Date: Jan. 20, 2000

(30) Foreign Application Priority Data

Jul. 9, 1998 (DE) .......................... 198 30 649

(51) Int. Cl.[7] .................. A61F 13/02; A61F 13/00; A61L 15/16; A61K 9/70
(52) U.S. Cl. ........................ 424/449; 424/448
(58) Field of Search .................. 424/449, 448

(56) References Cited

U.S. PATENT DOCUMENTS

| | | | |
|---|---|---|---|
| 4,390,520 A | * | 6/1983 | Nagai et al. ............ 424/448 |
| 4,460,369 A | * | 7/1984 | Seymour ............... 128/849 |
| 4,938,964 A | | 7/1990 | Sakai et al. |
| 5,154,922 A | * | 10/1992 | Govil et al. ............ 424/447 |
| 5,204,119 A | * | 4/1993 | Shiobara et al. ......... 424/449 |
| 5,252,334 A | * | 10/1993 | Chiang et al. ........... 424/443 |
| 5,474,783 A | | 12/1995 | Miranda et al. |
| 5,478,567 A | | 12/1995 | Nakagawa et al. |
| 5,702,720 A | | 12/1997 | Effing et al. |
| 5,869,087 A | * | 2/1999 | Hirano et al. ............ 424/449 |
| 6,156,335 A | * | 12/2000 | Rovati et al. ............ 424/448 |

FOREIGN PATENT DOCUMENTS

| | | |
|---|---|---|
| DE | 40 20 144 | 4/1994 |
| DE | 43 39 400 | 5/1995 |
| DE | 195 27 306 | 2/1997 |
| DE | 197 06 824 | 3/1998 |
| EP | 0319988 | 6/1989 |
| EP | 0 359 625 | 3/1990 |
| EP | 0 827 741 | 1/1992 |
| GB | 2 273 044 | 6/1994 |
| JP | 5-238931 | 9/1993 |
| WO | WO 95/31193 | 11/1995 |

\* cited by examiner

Primary Examiner—Gollamudi S. Kishore
Assistant Examiner—Todd D Ware
(74) Attorney, Agent, or Firm—D. Peter Hochberg; Katherine R. Vieyra; Sean Mellino

(57) ABSTRACT

A topical patch having non-steroid antirheumatic agent as active substance, consisting of a backing layer inert to the active substance, a self-adhesive, active substance-containing matrix layer based on a polyacrylate adhesive, and a protective film to be removed prior to use, is characterized in that a. the non-steroid antirheumatic agent has a free carboxyl group, b. the active substance-containing matrix of the patch consists of a polyacrylate adhesive cross-linked with multivalent metal ions and having free carboxyl groups, and is free of hydroxyl groups, c. the matrix contains a fatty acid as plasticizer and permeation enhancer, and d. the backing layer consists of a material that is elastic in at least one direction.

13 Claims, 2 Drawing Sheets

Results of Permeation Studies

TOPICAL PLASTER WITH NON-STEROIDAL ANTIRHEUMATIC AGENTS WITH AN ACID GROUP

BACKGROUND OF THE INVENTION

1. Field of the Invention

A large group of the so-called non-steroid antirheumatic agents are active substances which are to be considered derivatives of acetic acid and of propionic acid.

2. Description of the Prior Art

Examples of acetic acid derivatives are—without claim to exhaustiveness—indomethacin, acemetacine, tolmetin, diclofenac and lonazolac; examples of propionic acid derivatives (profens) are ibuprofen, flurbiprofen, fenoprofene, ketoprofen, naproxen and tiaprofen.

The free carboxyl group is significant to the action of this class of substances as it leads to accumulation of the active substances in inflammatory tissues having a decreased pH value.

For peroral administration, however, it is frequently not the free acids which are used but the salts, since these have better solubility in aqueous environment. For topical administration, however, the free acids are better suited since electrically neutral substances have a greater capability of penetrating the stratum corneum of the human skin than electrically charged salts.

As a side effect, the occurrence of stomach trouble and hemorrhages in the gastrointestinal region have been described for all of the above-mentioned substances. In the case of local complaints it is therefore advantageous not to administer these substances systemically but locally.

Such complaints are, for example, inflammatory-rheumatic diseases of the joints and the spinal column, swellings and inflammations of the soft tissue in the vicinity of joints, shoulder stiffness, low back pain, lumbago, as well as sports injuries and accidental injuries.

For local administration, gels, ointments or self-adhesive patch systems may be used, with the self-adhesive patch systems having the advantage over ointments and gels that they do not contaminate a person's clothing and that the patches—provided that they are correspondingly designed—must be applied only once every 1–2 days.

Such patches for topical application at the site of action typically consist of an active substance-containing, self-adhesive, so-called matrix layer, a—frequently textile—backing layer, and a protective layer—to be removed prior to use—for the matrix.

By reason of the action being only topical at the site of application, such patches have a size starting from about 70 $cm^2$ and reaching up to about 250 $cm^2$. This means that the physical properties of the backing layer are of great significance for the wearing characteristics of the patch. Especially in the case of application in the region of joints, it emerges that the backing layer must be elastic in one direction at least, in order to, on the one hand, have sufficient adherence in this region, and, on the other hand, to not excessively restrict freedom of movement. Film-type materials are either non-elastic or, if they are elastic, they are made of materials that are not inert to the ingredients of the matrix of the patch.

In addition, with films, the water vapor permeability in dependence on the selected materials frequently poses a problem since occlusion, and sweating, which is connected therewith, can significantly affect the adhesive properties.

Textile materials are also not without problems since materials such as cotton or polyurethane tend to bind active substances or diffusible auxiliary substances. Polyurethanes, in particular, tend to change their physical properties in an inadmissible manner.

The adhesive also has to fulfill specific requirements. Its most important function is to anchor the system safely on the skin for the time for which the patch is intended to be worn, without causing pain or leading to torn-off skin when the patch is removed. The adhesive should have no occlusive action since, as occlusion increases, skin compatibility is decreased. Since the adhesive has intimate contact with the active substance, it must be sufficiently inert thereto, in order to have a patch that is stable for at least two years. The composition of the adhesive must be appropriately geared to the given chemical composition of the active substances and auxiliary substances. Not least, the adhesive must have adequate solubility for the active substances. Since the permeation rate is fundamentally dependent on thermodynamic activity, one has to aim at an active substance concentration that is as near to the saturation concentration as possible.

Generally, by reason of the amount of active substance to be released being, after all, relatively large, one should aim at a solubility of at least 5% (w/w), and, for reasons of active substance economy, not more than 30%, better: not more than 15% (w/w).

All of these demands are best met by polyacrylate adhesives. These adhesives are produced by radical polymerization of acrylic or methacrylic acid, and their derivatives. Additionally possible monomers are vinyl compounds such as, for example, vinyl acetate or maleic acid.

Apart from the more technical aspects, skin compatibility is of great importance to topical systems. While systemically active transdermal therapeutic systems (TTS) are applied to varying skin areas, in the case of topical patches the application site is determined by the complaint. This means that in such patches only ingredients having good skin-tolerance can be used for the matrix. Moreover, the adhesive behavior must be adapted such that, on the one hand, the patch reliably adheres to the skin for the intended application time, and, on the other hand, no excessive mechanical irritation of the skin occurs when the patch is removed.

As a matter of course, the patches must be capable of releasing enough active substance in order to achieve sufficiently high tissue levels in the tissues lying underneath the patches, i.e. at the site of action.

It is likewise a matter of course that the administration form must meet the demand of having sufficient stability with respect to the active substance content, the release of active substance and the adhesive behavior.

In summary, topical patches should substantially fulfill the following requirements as optimally as possible:

sufficiently high permeation rate for obtaining therapeutically effective tissue levels at the site of application, good skin compatibility in the case of multiple application at the same site, good, but not too firm, adherence, and no stripping on removal, elasticity in at least one direction, to enable application in the joint region, stability for at least 2 years, simple and cost-effective production.

It is the object of the present invention to provide a topical patch with non-steroid antirheumatic agents having free carboxyl groups, which fulfills the above-mentioned requirements.

SUMMARY OF THE INVENTION

This object has surprisingly been solved, for the active substance group of the non-steroid antirheumatic agents having free carboxyl groups, by means of a patch comprising a backing layer made of a material that is elastic in at least one direction and is inert to the active substance, a self-adhesive, active substance-containing matrix layer containing fatty acid based on a polyacrylate adhesive, which is cross linked with multivalent metal ions and has free carboxyl groups, and a protective sheet to be removed prior to use. The matrix has one layer and is free of hydroxyl groups and the backing layer is made of an elastic polyester woven fabric or polyester knitted fabric, or a non-woven, woven or knitted fabric of polyethylene terephthalate, or a closed-cell, elastic foam.

In the patent literature, topical patches are described that also comprise non-steroid active substances. Patches based on hydrogels have not been taken into account since by reason of their low adhesive power their use without additional fixing bandages is limited.

GB 2 273 044 describes patches, for example, which also comprise ketoprofen as active ingredient. In these, the active substance is combined in the matrix with substances improving permeation through the skin, said substances belonging to the group of fatty acid esters, polyoxethylene derivatives, glycerides, fatty acid esters of propylene glycol, and pyrrolidone derivatives. The adhesive here can also be from the group of polyacrylate adhesives. Nothing is said about the physical properties of the backing layer. As a material for textile backing layers, cotton is mentioned, which, however, binds a large part of the active substance contained in the matrix, thereby having a negative influence on the active substance release.

Acidic functional groups, as well as the use of carboxyl group-containing plasticizers or permeation enhancers, are not described.

A topical patch comprising the active substance ketoprofen is described in DE-OS 195 27 306. This patch is characterized by a multi-layer matrix, with the individual layers having different water absorption capacity.

U.S. Pat. No. 5,702,720 describes a patch comprising flurbiprofen as active substance. The matrix of this patch also consists of a polyacrylate adhesive, containing polyvinylpyrrolidone as an additional component. Polyvinylpyrrolidone is to be regarded as disadvantageous in this context as this polymer exhibits strong interaction with carboxyl groups and phenolic OH groups. It does improve adherence to the skin, but at the price of a lower release of active substance or, respectively, a higher amount of active substance necessary in the patch.

In WO 95/31193 a patch comprising ibuprofen as active substance is described. Here, the matrix consists of two different polyacrylate polymers and—besides the active substance—additionally of diethyl phthalate. Diethyl phthalate, in this context, cannot be considered toxicologically safe as it is capable of penetrating the skin in considerable amounts. An acidic plasticizer in conjunction with acidic functional groups in the matrix and with a non-steroid antirheumatic agent having free carboxyl groups has not been described.

None of the patches mentioned in the prior art contains all of the elements in an optimized form that are necessary for a topical patch.

It was surprising that the combination of an active substance having a free carboxyl group with a cross-linked acrylate adhesive—from the polymerized acrylic or methacrylic acid—having free carboxyl groups, and a fatty acid as plasticizer and permeation enhancer, should result in a matrix whose physical properties would optimally comply with all the requirements.

The cross-linking of the acrylate adhesive is carried out with multivalent metal cations, preferably with aluminium, the aluminium ions being added to the solution of adhesive as aluminium acetyl acetonate. The organic portion of the compound is removed along with the solvents when the adhesive is dried; the carboxyl groups of the adhesive now form the counter ions to the aluminium cations. The resultant crosslinking is to be regarded as reversible. Obviously, both the acid active substance and the acid plasticizer also enter into interaction with the aluminium ions, thereby providing the matrix with good adhesion behavior without said matrix becoming too soft and thereby becoming prone to so-called "cold flow".

This cold flow on the one hand constitutes a stability problem, on the other hand it has the disturbing effect that after the patch has been removed from the skin, margins of adhesive remain on the skin.

Further, it is to be expected that the fatty acid present will block those sites in the polymer which can also interact with the acidic active substance and which may thus affect the release properties of the acidic active substance. A further advantage lies in the fact that by the presence of the fatty acid, the dissociation of the active substance acid is restrained in favor of the neutral active substance acid, thereby favoring the neutral form of the active substance, which is better capable of permeating the skin.

In all, there is thus a plurality of influences, interacting with one other, which in their combination provide the matrix with optimal physical properties.

The backing layer of the patch consists of a polyester woven fabric or polyester knitted fabric which is elastic at least in one direction, or of an elastic closed-cell foam.

These polyester woven or knitted fabrics gain their elasticity through the elasticity of the polyester yarns used. They are thereby different from slightly elastic polyester non-wovens. Such non-wovens are available but have the disadvantage that they are only sufficiently elastic if they are very thin, but then they do no longer sufficiently cover the self-adhesive matrix and provide protection against conglutination with the packaging material, or the clothing when the patch is being worn. Polyester woven or knitted fabrics, even when very thick (about 150 g/m$^2$), have an extensibility which is sufficient for their use as textile backing layers of patch systems. The main advantage of using polyester, however, lies in the fact that of all the materials conceivable for such woven or knitted fabrics, polyester is the material most inert to diffusible ingredients of the matrix. It thereby stands out above all in comparison to materials such as cotton, viscose, polyamides or polyvinyl acetates. Even after 3-years' storage, the release rate of a patch, as proven in the Example of ibuprofen and ketoprofen, remains unchanged if a backing layer of polyester is used (see Table 1). It follows from that that no active substance whatsoever is absorbed by this material.

The active substance content itself also remains constant over this period even where the patch is stored at increased temperatures. No degradation products are observed. This is an additional proof of the excellent stability of such patches.

As in vitro permeation tests on human epidermis prove, the active substance release to the skin is sufficiently high, too. By way of example, this is shown in permeation tests with patches that were prepared according to Examples 2 and 3.

It is possible to increase the permeation rate further by using a backing layer of a closed-cell foam based on polyethylene, polypropylene, polyvinyl chloride or a copolymer of ethylene and vinyl acetate. The reason for this is an increase in occlusion, which generally has an increasing effect on the permeation rate. By using such foams as a backing layer one does not, it is true, obtain the high elasticity and the same wearing comfort as when using polyester wovens, but one has the advantage of higher efficacy by reason of the higher release rates of the patch for the active substance.

DESCRIPTION OF THE PREFERRED EMBODIMENT

Figure 1:
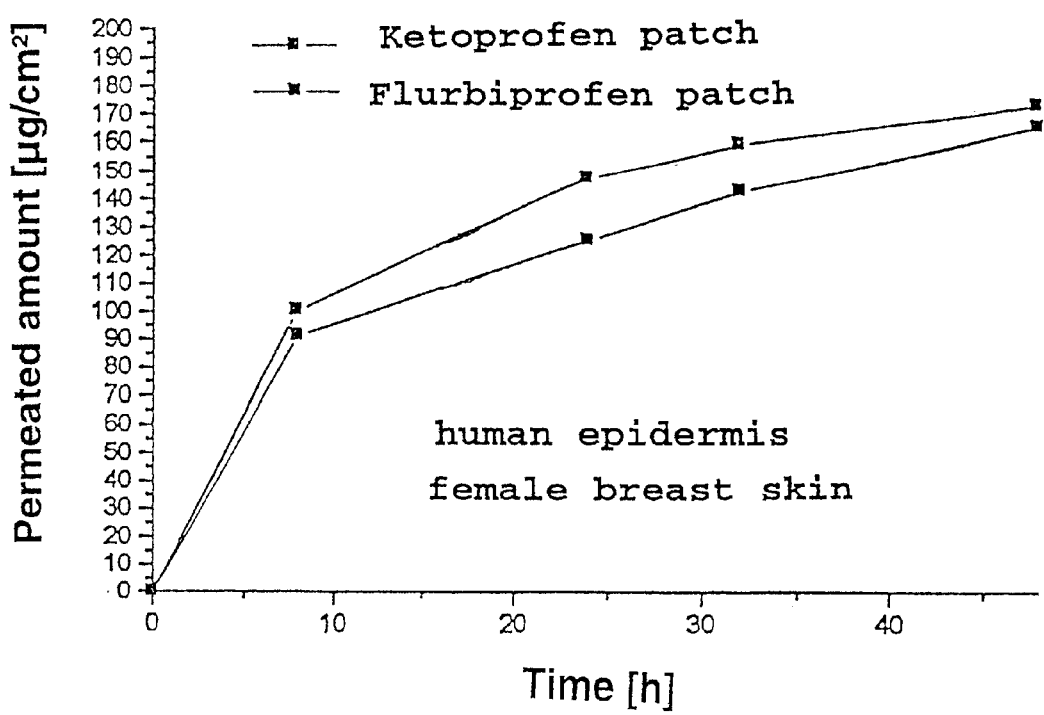
FIG. 1 is a graph of permeation results, obtained from in vitro permeation studies on human epidermis, using the generally known Franz Diffusion Cell.
Figure 2:
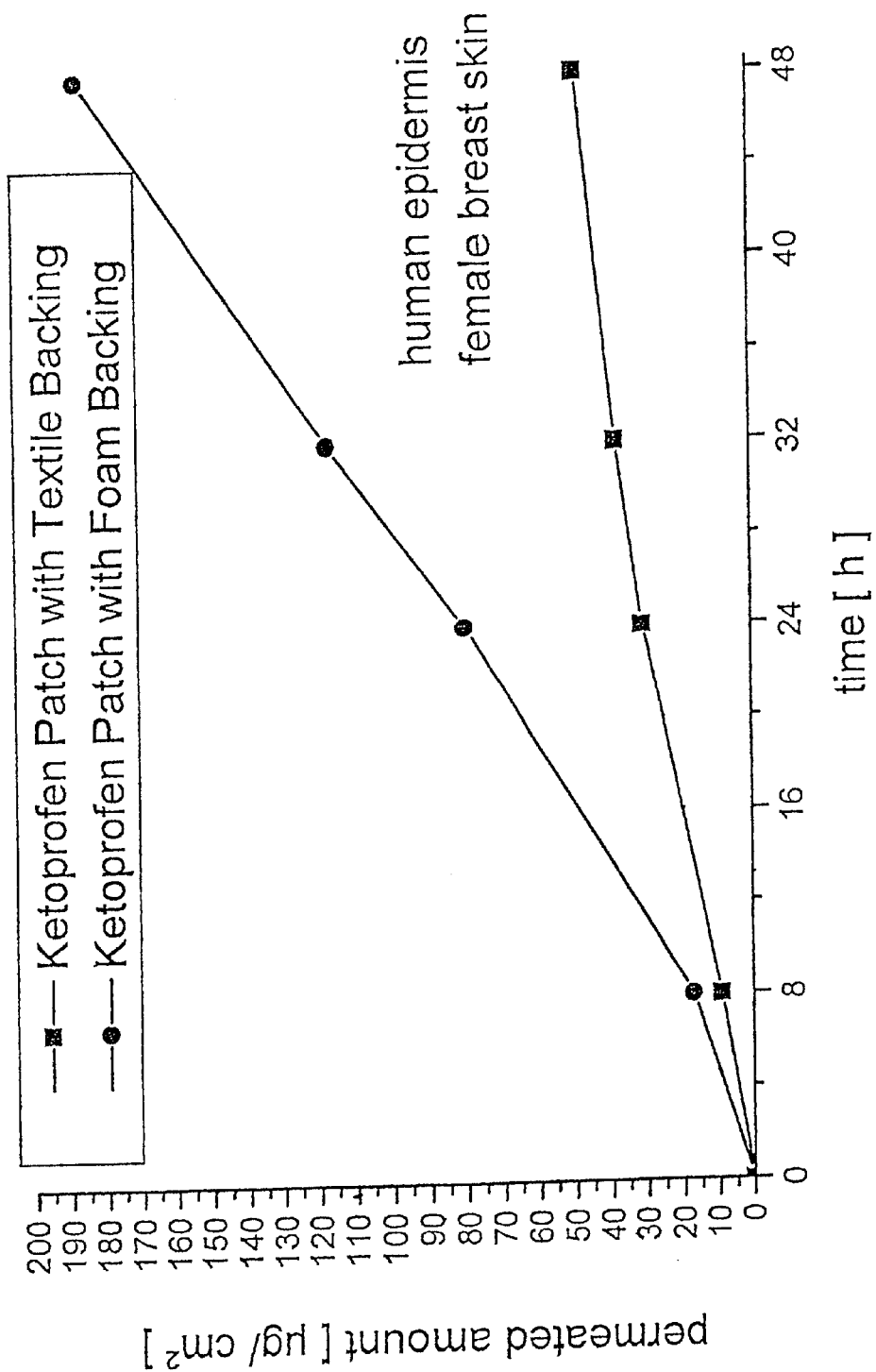
FIG. 2 is a graph verifying the higher permeation rate by means of comparative permeation studies using human epidermis, for the active substance ketoprofen (by way of example).

The preparation of patches in the sense of the invention is illustrated by the Examples 1 to 3. This manner of preparation can be adopted for all non-steroid active substances having acid groups, it being necessary, however, to find the suitable concentration for each individual active substance.

EXAMPLE 1

Patch With Ketoprofen as Active Substance

To 500 g of Durotak 387-2251 having a solids content of 48%-wt. are added 58 g of oleic acid and 26 g of ketoprofen, and this is stirred until all of the ketoprofen has been dissolved.

Subsequently, 90 g of a 4% (w/w) solution of aluminum acetyl acetonate are added, and the solution is homogenized by stirring.

Thereafter, to prepare the matrix layer, the solution is coated onto a siliconized film, and the solvents are removed by drying for 20 minutes at 50° C. The coating thickness is selected such that the dried matrix film has a coating weight of 80 g/m$^2$.

The dried matrix layer is then laminated with a woven fabric of polyester which is elastic in two directions; from the resultant total laminate, the finished patches are punched out.

EXAMPLE 2

To 500 g of Durotak 387-2251 having a solids content of 48%-wt. are added 58 g of oleic acid and 30 g of flurbiprofen, and this is stirred until all of the flurbiprofen has been dissolved.

Subsequently, 90 g of a 4% solution of aluminum acetyl acetonate are added, and the solution is homogenized by stirring.

Thereafter, to prepare the matrix layer, the solution is coated onto a siliconized film, and the solvents are removed by drying for 20 minutes at 50° C. The coating thickness is selected such that the dried matrix film has a coating weight of 80 g/m$^2$.

The dried matrix layer is then laminated with a woven fabric of polyester which is elastic in two directions; from the resultant total laminate, the finished patches are punched out.

EXAMPLE 3

Patch With Ibuprofen as Active Substance

To 500 g of Durotak 387-2251 having a solids content of 48%-wt. are added 58 g of oleic acid and 41 g of ibuprofen, and this is stirred until all of the ibuprofen has been dissolved.

Subsequently, 90 g of a 4% solution of aluminum acetyl acetonate are added, and the solution is homogenized by stirring.

Thereafter, to prepare the matrix layer, the solution is coated onto a siliconized film, and the solvents are removed by drying for 20 minutes at 50° C. The coating thickness is selected such that the dried matrix film has a coating weight of 150 g/m$^2$.

The dried matrix layer is then laminated with a woven fabric of polyester which is elastic in two directions; from the resultant total laminate, the finished patches are punched out.

The invention has been described with particular emphasis on the preferred embodiments, but variations and modifications within the spirit and scope of the invention may occur to those skilled in the art to which the invention pertains.

I claim:

1. Topical patch containing as active substance a non-steroid antirheumatic agent having a free carboxyl group, comprising:
    a backing layer inert to the active substance, which backing layer is made of a material that is elastic in at least one direction;
    a self-adhesive, active substance-containing matrix layer consisting of a polyacrylate adhesive, which polyacrylate adhesive is crosslinked with multivalent metal ions and comprises free carboxyl groups, the said matrix containing a fatty acid; and
    a protective sheet to be removed prior to use,
    wherein said backing layer is made of at least one of an elastic polyester woven fabric or polyester knitted fabric, a nonwoven, a woven or a knitted fabric of polyethylene terephthalate, and a closed-cell, elastic foam, and said matrix comprises one layer and is free of hydroxyl groups.

2. Topical patch according to claim 1, wherein the non-steroid antirheumatic agent is a profen derivative.

3. Topical patch according to claim 1, wherein the active substance is selected from the group consisting of ketoprofen, ibuprofen, flurbiprofen and naproxen.

4. Topical patch according to claim 3, wherein the active substance is ketoprofen and is contained in the matrix of the patch in a concentration between 5 and 15%-wt.

5. Topical patch according to claim 4, wherein said active substance is contained in said matrix in a concentration between 6 and 10%-wt.

6. Topical patch according to claim 3, wherein the active substance is flurbiprofen and is contained in said matrix in a concentration between 5 and 15%-wt.

7. Topical patch according to claim 1, wherein the fatty acid is selected from the group consisting of oleic acid, linoleic acid and linolenic acid.

8. Topical patch according to claim 1, wherein the fatty acid is oleic acid and said fatty acid is present in said matrix in a concentration between 5 and 20%-wt.

9. Topical patch according to claim 1, wherein the polyacrylate adhesive has been produced by radical polymerization, said polymerization reaction including the polymerization of at least 2-ethylhexyl acrylate and acrylic acid.

10. Topical patch according to claim 1, wherein the polyacrylate adhesive has been produced by radical polymerization, said polymerization reaction including the polymerization of at least 2-ethylhexyl acrylate, vinyl acetate, acrylic acid, butyl acrylate.

11. Topical patch according to claim 1, wherein the backing layer consists of a polyethylene terephthalate woven fabric which is elastic in two directions.

12. Topical patch according to claim 1, wherein the closed-cell foam comprises at least one of polyethylene, polypropylene, polyvinyl chloride and a copolymer of ethylene and vinyl acetate.

13. Topical patch containing as active substance a nonsteroid antirheumatic agent having a free carboxyl group, comprising:

a backing layer inert to the active substance, which backing layer is made of a material that is elastic in at least one direction;

a self-adhesive, active substance-containing matrix layer comprising a polyacrylate adhesive, which polyacrylate adhesive is crosslinked with multivalent metal ions and comprises free carboxyl groups, the said matrix containing a fatty acid; and a protective sheet to be removed prior to use, wherein said backing layer is made of at least one of an elastic polyester woven fabric or polyester knitted fabric, a nonwoven, a woven or a knitted fabric of polyethylene terephthalate, and a closed-cell, elastic foam, and said matrix comprises one layer and is free of hydroxyl groups.

* * * * *

UNITED STATES PATENT AND TRADEMARK OFFICE
CERTIFICATE OF CORRECTION

PATENT NO.    : 6,676,962 B1
DATED         : January 13, 2004
INVENTOR(S)   : Walter Müller It is certified that error appears in the above-identified patent and that said Letters Patent is hereby corrected as shown below:

Title page,
Item [86], 371 Date, should be -- March 9, 2001 --.

Signed and Sealed this

Fourth Day of May, 2004

JON W. DUDAS
*Acting Director of the United States Patent and Trademark Office*